United States Patent
Grefve et al.

(10) Patent No.: US 6,668,626 B2
(45) Date of Patent: Dec. 30, 2003

(54) SYSTEM AND A METHOD FOR MEASURING AND DETERMINING FLATNESS

(75) Inventors: Kenneth Grefve, Västerås (SE); Jörgen Bosson, Västerås (SE); Magnus Hallefält, Kvicksund (SE); Lars Jonsson, Västerås (SE)

(73) Assignee: ABB AB, Vasteras (SE)

( * ) Notice: Subject to any disclaimer, the term of this patent is extended or adjusted under 35 U.S.C. 154(b) by 0 days.

(21) Appl. No.: 10/083,652

(22) Filed: Feb. 27, 2002

(65) Prior Publication Data

US 2002/0134146 A1 Sep. 26, 2002

Related U.S. Application Data

(60) Provisional application No. 60/272,051, filed on Mar. 1, 2001.

(51) Int. Cl.$^7$ ................................. B21B 37/28
(52) U.S. Cl. ......................... 73/104; 72/9.1; 72/18.7
(58) Field of Search ......................... 73/104, 105, 159, 73/862.07; 72/8.7, 9.1, 7.2, 7.6, 8.9, 18.7, 31.01, 31.05, 11.7, 205

(56) References Cited

U.S. PATENT DOCUMENTS

| | | | | |
|---|---|---|---|---|
| 2,809,519 A | * | 10/1957 | Kaestner | 73/159 |
| 3,481,194 A | * | 12/1969 | Sivilotti et al. | 73/862.07 |
| 3,703,097 A | * | 11/1972 | Kilpatrich et al. | 73/159 |
| 3,826,132 A | * | 7/1974 | Fetner et al. | 73/862.391 |
| 3,850,024 A | * | 11/1974 | Ando et al. | 73/37.7 |
| 3,902,363 A | | 9/1975 | Ishimoto | 73/159 |
| 4,024,755 A | * | 5/1977 | Quehen | 73/105 |
| 4,289,005 A | * | 9/1981 | Cabaret et al. | 72/8.7 |
| 4,356,714 A | | 11/1982 | Quehen | 72/17 |
| 4,428,244 A | * | 1/1984 | Takeda | 73/862.07 |
| 4,463,586 A | * | 8/1984 | Griffin | 72/11.7 |
| 4,470,297 A | * | 9/1984 | Ruhl | 73/159 |
| 4,512,170 A | * | 4/1985 | Hsu | 72/11.7 |
| 4,860,212 A | | 8/1989 | Uesugi | 364/472 |
| 4,972,706 A | * | 11/1990 | Adolfsson et al. | 73/159 |
| 5,537,878 A | * | 7/1996 | Sendzimir et al. | 73/862.391 |
| 5,557,100 A | * | 9/1996 | Jeuniaux et al. | 250/227.16 |
| 5,693,893 A | * | 12/1997 | Anabuki et al. | 73/862.07 |
| 6,212,960 B1 | | 4/2001 | Durand-Texte et al. | 73/862.07 |
| 6,354,013 B1 | * | 3/2002 | Mucke et al. | 33/533 |
| 2002/0014099 A1 | * | 2/2002 | Norikura | 72/12.7 |

FOREIGN PATENT DOCUMENTS

| | | |
|---|---|---|
| DE | 38 30 629 A1 | 3/1990 |
| DE | 196 09 135 A1 | 9/1997 |
| EP | 1 048 370 A2 | 11/2000 |

\* cited by examiner

Primary Examiner—Hezron Williams
Assistant Examiner—David A. Rogers
(74) Attorney, Agent, or Firm—Dykema Gossett PLLC (57) ABSTRACT

A system and a method for measuring and determining flatness of a strip (1) of rolled material. Said system is comprising a measuring roll (2) having a cylindrical central structure (41) having a number of measuring devices for force/pressure registration. Said devices is generating measurement output signals ($U_{pi}$) depending on the contact between the strip and the measuring roll (2), wherein said measurement output signal ($U_{pi}$) comprises a force component signal ($U_{Fi}$). Said system also comprises a Flatness Determination Unit (56), said unit being arranged for calculating the flatness ($\Delta\sigma_1$) of the strip based exclusively on signals derived from measurement output signal ($U_{pi}$) values generated by said measuring devices and information about the values of the width and thickness of the strip (1). The system is continuously determining the Wrap Angle ($\alpha$) from at least one measurement output signal ($U_{pi}$) and automatically compensating for a changing Wrap Angle ($\alpha$). The present invention also provides a computer program product, a computer data signal and a flatness determination signal for accomplishing said objects of the invention.

23 Claims, 5 Drawing Sheets

SYSTEM AND A METHOD FOR MEASURING AND DETERMINING FLATNESS

CROSS REFERENCE TO RELATED APPLICATIONS

This application is related to U.S. provisional application Serial No. 60/272,051, filed Mar. 1, 2001, the teachings of which are incorporated herein by reference.

TECHNICAL AREA

The invention relates to a measuring system and method for continuous production of substantially long and flat sheet or strip of material such as copper, steel or aluminium. More particularly it is a system, a computer program product, a computer data signal, a flatness determination signal and a method for flatness measuring for use in a rolling mill.

BACKGROUND ART

In the rolling of strip and sheet materials it is common practice to roll a material to desired dimensions in a rolling mill stand and then feed the resulting strip to a coiler. On the coiler, the strip is wound up into a coil. Such coils are then taken off the coiler and after some time has elapsed moved on to subsequent processes such as annealing, slitting, surface treatment processes, or other processes.

The tension in the strip between a mill stand and a coiler is carefully monitored and it is known to measure tension distribution across a strip in order to regulate the flatness of the rolled material. In U.S. Pat. No. 3,481,194 Sivilotti and Carlsson disclose a strip flatness sensor. It comprises a measuring roll over which the strip passes between a mill stand and, for this example, a coiler. The measuring roll detects the pressure in a strip at several points across the width of the strip. The pressure represents a measure of the tension in the strip. The measurements of tension in the strip result in a map of flatness in each of several zones across the width of the strip. U.S. Pat. No. 4,400,957 discloses a strip or sheet mill in which tensile stress distribution is measured to characterise flatness. The measures of flatness are compared to a target flatness and a difference between measured flatness and target flatness is calculated, as a flatness error. The flatness error is fed back via a control unit to the actuators of the mill stand, so as to regulate and control flatness in the strip in order to approach a zero flatness error.

Different sensors, gauges, and/or transducers generate input values to a system for flatness measurement. Said system comprises different measurement systems or blocks for determining quantities like strip tension, distributed force, and finally flatness.

The quantity strip tension is a measured value corresponding to the force of the strip against the measuring roll. Said force is registered by means of tensiometer load cells, which are fixed at shaft bearings of the measuring roll. Strip tension is an important quantity for determining the average force on the roller and on each measuring device.

Some necessary input quantities, like the wrap angle of the strip over the measuring roll, have not been determined by means of any measuring devices. They have been pre-loaded into the system and if a value is changing during the process it has been adjusted for an example, by calculation. In U.S. Pat. No. 3,481,194 Sivilotti and Carlsson prescribe a certain angle for the passing of the strip over the measuring roll. The wrap angle is an important value when calculating other values of interest. It is used for calculating the Distributed Force per sensor on the measuring roll. The wrap angle depends on the radius of the coil on the coiler. The wrap angle will change when the radius of the coil grows and, therefore, the value of the wrap angle has to be adjusted during the process.

As shown above, prior art systems comprise different sensors for registering and measuring different quantities and, as a consequence thereof, different measurement blocks corresponding to said quantities. Said systems are quite complex and expensive. The cost for construction and support increases rapidly with growing complexity and increasing number of different systems and sensing devices like sensors and transducers.

Thus, a system for measuring flatness having less different details, but still able to generate at least the same result as a prior art system, is preferable.

SUMMARY OF THE INVENTION

It is an object of the invention to provide a flatness measuring system using measurement output signals only generated at the contact surface of a measuring roll and not elsewhere, e.g. at the shafts, for flatness determination and calculation. It is further an object of the invention to suggest a flatness measuring system comprising less number of different sensing devices and system blocks. It is another object of the invention to suggest a flatness measuring system and method wherein the wrap angle is continuously measured and determined. It is a further object of the invention to reduce the number of necessary input signals. It is a yet further object of the invention to provide a system and a method to measure the flatness of a strip. It is yet another object of the invention to provide a more correct value of the flatness.

The invention may be described as a flatness measuring and determining system and method in which flatness of a given strip is of rolled material, comprising a measuring roll, having a number of force/pressure sensors/transducers that are situated in a certain pattern on said roll, each sensors/transducer generating an measurement output signal $U_{pi}$ depending on the pressure of the flat sheet on to the transducer/sensor and a Wrap Angle $\alpha$ of the strip on the measuring roll. Said system also comprises a Flatness Determination Unit, said unit being arranged for calculating a Wrap Angle value based on said measurement output signals, and, based thereon, the flatness of the strip. The present invention also provides a computer program product, a computer data signal and a flatness determination signal for accomplishing said objects of the invention.

The main advantage of the invention is that the system contains a reduced number of different measuring blocks and different sensors/transducers.

Another advantage is that the system is not so complex and expensive. A further advantage is that the system uses a measured value of the Wrap Angle and not an estimated value and therefore the system will provide a more correct value of the flatness.

BRIEF DESCRIPTION OF THE DRAWINGS

The present invention will be described in more detail in connection with the enclosed drawings.

DESCRIPTION OF THE PREFERRED EMBODIMENTS

Figure 1:
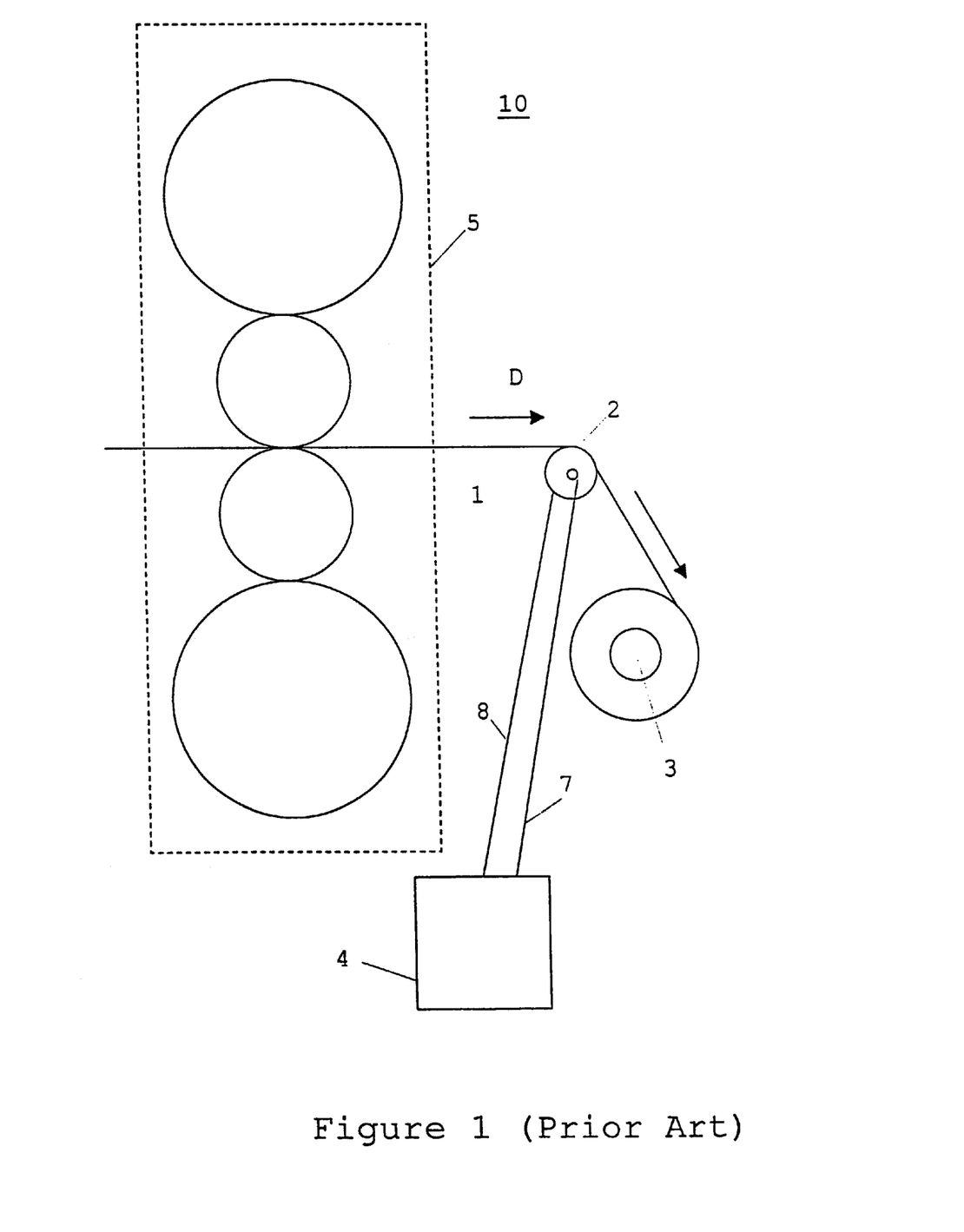
FIG. 1 (Prior art) shows schematically a part of a rolling mill including a flatness measuring roll, a mill stand and a coiler according to the known art.

In order to explain the invention, a rolling mill system 10 in the prior art will first be described in summary detail. FIG. 1 (Prior art) shows a metal strip 1 passing through a mill stand 5 in a direction shown by an arrow D. Strip 1 passes over a measuring roll 2 to a coiler 3. Measurement signals from the load cells at the shaft bearings of the measuring roll 2 are connected to the flatness measuring unit 4 via a first measurement connection 7. Measuring devices on the measuring roll 2 are coupled to a flatness measuring unit 4 via a second measurement connection 8. Measurements of the strip corresponding to strip flatness are taken on exit from mill stand 5 by measuring roll 2 before coiling the strip on coiler 3.

Figure 2:
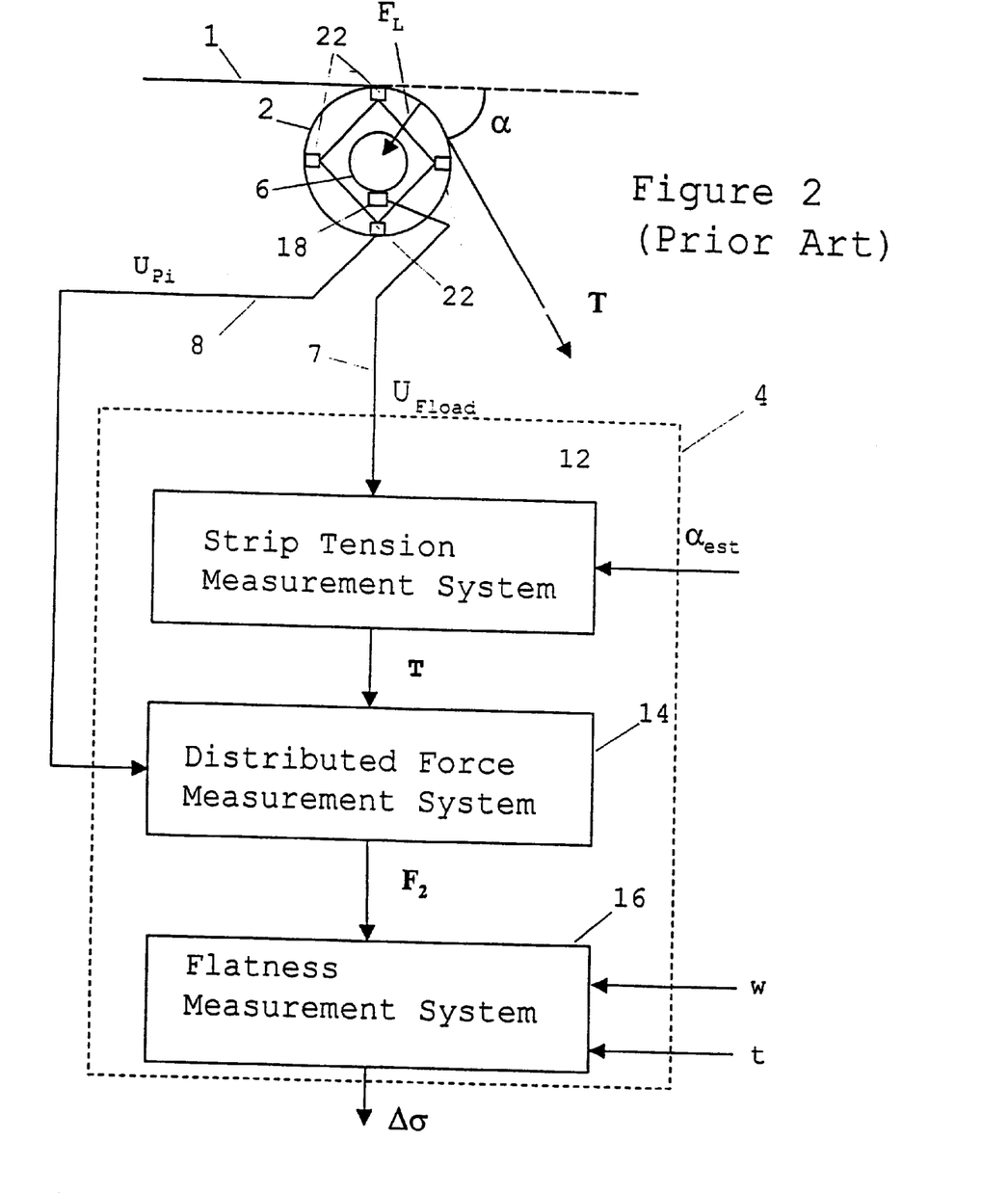
FIG. 2 (Prior art) shows a simplified block diagram for measuring flatness according to the known art.

FIG. 2 (Prior art) shows a simplified block diagram for a known system for a flatness measuring unit 4. Said system comprises a Strip Tension Measurement System 12, a Distributed Force Measurement System 14 and a Flatness Measurement System 16. The Strip Tension Measurement System (STMS) 12 is electrically connected to tensiometer load cells 18, which are fixed at the shaft bearings 6 of a measuring roll 2. The load cells 18 generates an input signal $U_{Fload}$ that is transmitted over a first measurement connection 7 to the STMS. Said input signal $U_{Fload}$ is a measured value corresponding to the force $F_L$ of the strip against the measuring roll 2. For calculating Strip Tension T, a value for the current Wrap Angle α of the strip over the roll 2 is needed. The Wrap Angle α changes with the increased radius of the coil and the system uses an estimate value $α_{est}$ for the Wrap Angle. Said estimate value $α_{est}$ and load cell generated value $U_{Fload}$ is used for calculating the strip tension T [N]. The calculated value T is transmitted to Distributed Force Measurement System (DFMS)14. The measuring roll (2) has a number of force/pressure sensors/transducers (22) that are situated in a certain pattern on said roll. Each sensor/transducer generates an measurement output signal ($U_{pi}$) depending on the pressure of the flat sheet on to the transducer/sensor. The measurement signals are transmitted to the DFSM 14 via the second measurement connection 8. The DFSM 14 uses the strip tension T and each sensor/transducer signal for determining the Distributed Force $F_2$ per sensor/transducer. The determined value $F_2$ is transmitted to Flatness Measurement System (FMS) 16 for determining the Measured Flatness Δσ [N/mm²]. The width w and the thickness t, either a one- or multiple-dimensional vector, of the system has to be pre-loaded into the FMS.

Flatness per zone across the width of the strip during rolling is determined by means of the measuring roll 2, which has a number of force/pressure sensors that are situated in a certain pattern on said roll. A zone of the roll is a ring formed sector that is parallel with the rotational axle of the roller. Each measurement zone has at least one sensor/transducer and each sensor generates an measurement output signal depending on the pressure of the flat sheet on to the sensor/transducer. The sensors 22 are distributed on the roll in a special pattern. The flatness of the strip 1 will be mapped in parallel lines across the strip perpendicular to the movement direction. If there is a bump or irregularity in the strip, the sensors that come in contact with the bump will register a signal amplitude that differs from the average value generated from other parts of the strip.

Figure 3:
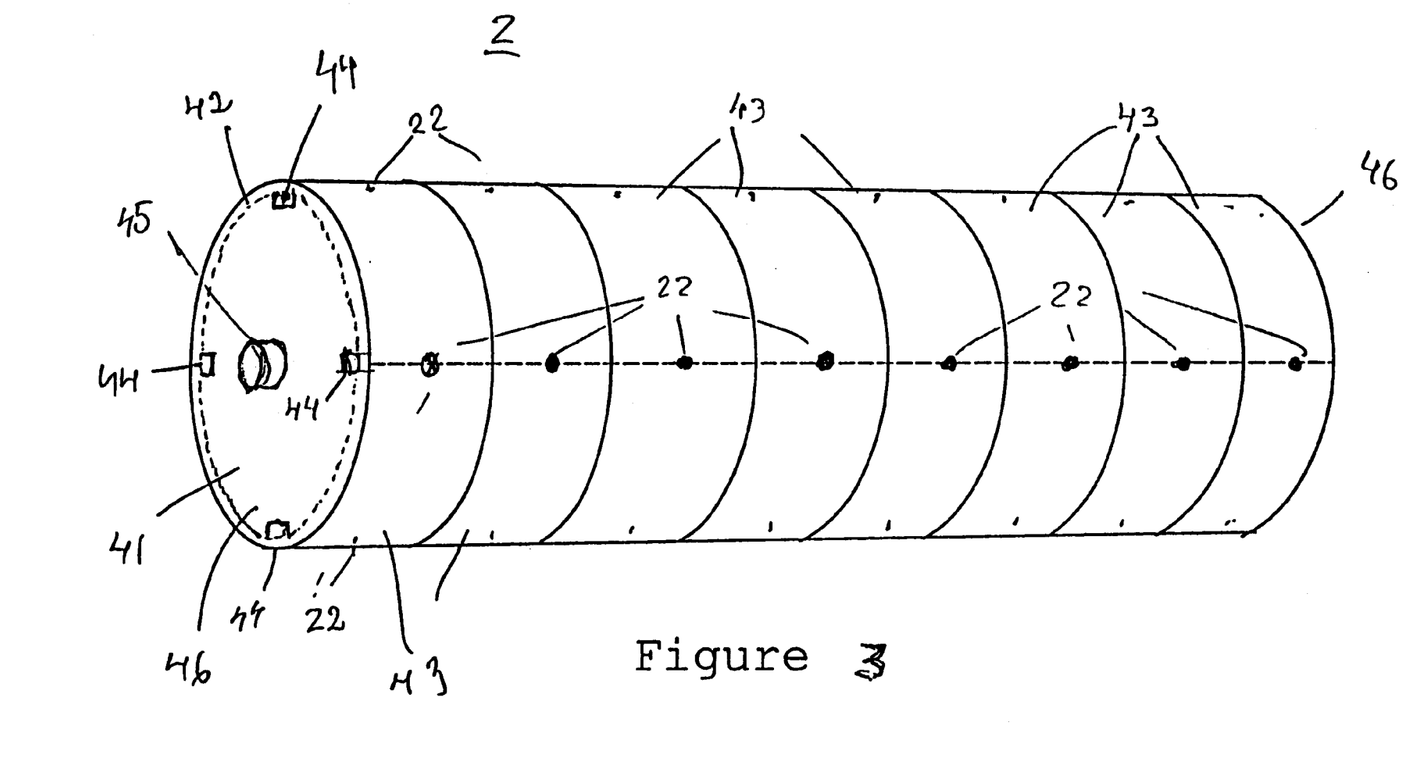
FIG. 3 illustrates a measuring roll.

In FIG. 3 an embodiment of a measuring roll 2 is illustrated. It comprises a cylindrical central structure 41, a strip contact device 42 and shaft taps 45. The strip contact device 42 is tightly attached to the structure 41, both having a circular cross-section. The strip contact device 42 of the measuring roll 2 is divided into a number of measurement zones 43, i (i=1,2,3 . . . , n),. All measurement zones together define a measurement area of the measuring roll 2. Each zone 43 may correspond to one strip contact ring and all rings together will constitute the strip contact device 42. Each zone 43 is annular and comprises a number of sensors 22. The sensors 22 are located in parallel slots 44. The strip contact device 42 comprise metal rings that covers and protects the sensors. The end parts 46 of the measuring roll 2 have a shaft tap 45.

However, the invention is not limited in its use to this described embodiment of measuring roll.The measuring roll 2 may have the force/pressure sensors distributed and organized in any known or unknown pattern on said roll and the measurement zones may have another distribution along the roll. The borders of the zones may be crossing the sensors.

Figure 4:
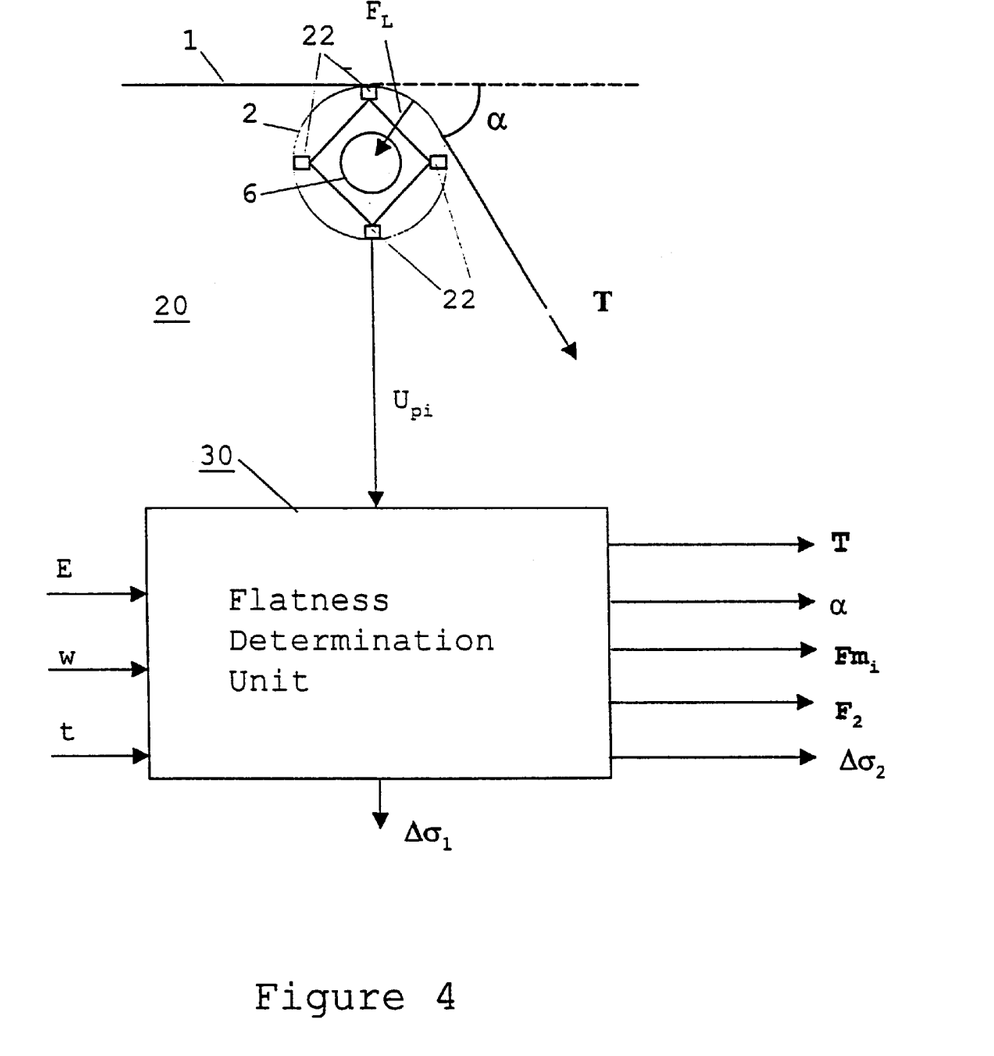
FIG. 4 shows a simplified block diagram of a preferred embodiment according to the invented system.

A preferred embodiment according to the invented system will now be described by means of FIG. 4.

Measuring devices comprises force/pressure transducers/sensors/gauges of known types will in the following of this description be denoted as force/pressure sensor or only sensor.

A system 20 for measuring flatness of a strip 1 of rolled material comprises a measuring roll 2, which has a number of force/pressure sensors 22 that are situated in a certain pattern on said roll. Each sensor 22 generates an measurement output signal $U_{pi}$ depending on the pressure of the flat sheet on to the sensor and a Wrap Angle α of the strip on the measuring roll 2. Said system 20 also comprises a Flatness Determination Unit 30, which is arranged for calculating a value corresponding the Wrap Angle α based on said measurement output signals $U_{pi}$ and, based thereon, the flatness of the strip.

A flatness determination signal may be derived from at least one measurement signal $U_{pi}$. As mentioned herein above, each separate measurement signal $U_{pi}$ is generated by a corresponding measuring device of all measuring devices belonging to at least one of all measurement zones of a measuring roll and comprises one or more measurable values for calculating at least one of following quantities or vectors: strip tension vector T, Wrap Angle α distributed force vector $F_2$, force vector $F_{mi}$, flatness vector $Δσ_1$ [N/mm²], and/or a corresponding quantity flatness vector $Δσ_2$ [I-unit]. The flatness determination signal is an input signal to a flatness determination unit for calculating at least one of said quantities or vectors. The flatness determination signal comprises a force component signal ($U_{Fi}$) and said force component signal ($U_{Fi}$) includes a train of electrical pulses.

A flatness determination signal may be derived by a number of said separate measurement signals $U_{pi}$. Each of said measurement signals includes a train of electrical pulses, which are synchronized and combined to a flatness determination signal for calculating at least one of said quantities or vectors. Different known techniques for combining such signals are possible, for example integration, signal addition, signal subtraction, etc.

The generated signals $U_{pi}$ or the derived flatness determination signals are input signals to the Flatness Determination Unit 30 for calculating the quantities Wrap Angle α, the force vector $Fm_i$ for the corresponding measurement zone, Strip Tension T and Distributed Force $F_2$ on each sensor/transducer, which quantities are used for calculating the flatness $\Delta\sigma_1$ and $\Delta\sigma_2$ corresponding to relative strain in I-unit by means of the Flatness Determination Unit 30. No tensiometer measurement load cells located elsewhere, e.g. fixed at the shaft bearings of a measuring roll shaft, are needed for determining the strip force on the measuring roll in the new invented system and all the above listed quantities are provided as output values.

The generated signals $U_{pi}$ or the derived flatness determination signals could be characterised as a computer data signal. The signals may be superimposed on a carrier waves for transmission of the signal values and characteristics from the sensors to a signal processing unit for separating and determining said signal values and characteristics, e.g. a value for calculating a flatness vector according to any of $\Delta\sigma_1$, $\Delta\sigma_2$.

In the following the Flatness Determination Unit, FDU, of a system 50 according to the invention will be described with reference to FIG. 5. As long as each zone and corresponding output signals are treated separately and no mixing or integration over the zones is performed by the system all measurement zones, channels and signal paths of the system are parallel and designed exactly in the same way. Therefore, in the following only one signal path of the measurement system will be described.

Every time a sensor is influenced by the strip passing a voltage or/and current is generated. The input signal to the sensor has a frequency $f_c$. When a force is applied to the measuring roll the input signal becomes a carrier wave that is modulated in proportion to the applied force. The signal may be sampled before it is transmitted to the FDU.

Each sensor, having no contact with the strip, will generate a noise signal. The FDU has synchronising circuits that generate synchronise pulses indicating the beginning and the end of a time period, called a time slot, during which the contribution from sensors that are in contact with the strip will be integrated. During the time interval when the sensors have no contact with the strip the noise signals will be neglected. The clock circuits also generate clock pulses for synchronisation of the different blocks and processes of the system.

Measurement signals, analogue or digital, will be transmitted from the measurement zones of the measuring roll 52 via the channels 54 to the FDU 56. The FDU 56 will have one input port and one signal treatment device 58 for each channel 54. In this embodiment, the force signal is Amplitude Modulated (AM) on a carrier wave having the carrier frequency $f_c$. However, a person skilled in the art can chose and apply any transmission method, such as any other modulation method or a method wherein no modulation is done.

One of the tasks of the signal treatment device 58 is to demodulate the input signal. Other signal operations carried out by the signal treatment device 58 are filtering and rectifying.

By multiplying an AM input signal with a rectification signal the input signal will be demodulated. After demodulation, the signal comprises both the force signal component $U_{Fi}$, a DC component and the carrier wave. The only useful signal is the force signal component $U_{Fi}$. A connected standard filter will remove the DC component. The signal treatment is finished and the force signal component $U_{Fi}$ is forwarded to the signal processing unit 60 or, shorter, signal processor, of the FDU 50.

The method and signal processing unit 60 for determining different quantities out of the signal treated force signal component $U_{Fi}$ will now be described in more detail.

The output of the signal treatment device 58 is a force signal component $U_F$ consisting of force pulses. Each pulse of the force signal component contains information about the force and wrap angle. The amplitude Â of each pulse is dependant on the force against the signal generating sensor 22 and the length of each pulse is dependent on the Wrap Angle α and the strip velocity. The Wrap Angle α determines the length of the strip contact area against the measuring roll and the velocity determines the time for a sensor to pass that area.

The first step 151 is to extract and determine the force vector $Fm_i$ for the corresponding measurement zone i, i=1,2,3, . . . ,n and the Wrap Angle α. This step, 151, is accomplished by a quantity processor block 62. The quantities $Fm_i$ and α are forwarded in digital form as signals to a tension processor block 64 that, in step 152, calculates the tension T [N] over the strip by generating the sum of force vectors $Fm_i$ for all measuring zones. Said sum is divided by the Sine of the Wrap Angle α, in accordance with the formula $$T = \Sigma Fm_i/(2 \sin \alpha/2)$$

The quantities T, α, and $Fm_i$ are forwarded in digital form as signals to separate output ports 266, 268, and 270 for further purposes in the rolling mill system, e.g. display. T is also transmitted to a Flatness Processor 74 that will be described further down in this description. The force vector $Fm_i$ is forwarded to an edge compensator 68 in the next step 153. Said device/block 68 introduces the width w of the strip and if necessary, the strip position on the measuring roll. The width of the strip varies and for determining the correct flatness value and tension and force distributions, the width variation must be considered. The result of the this calculation is the force distribution vector $F_2$ [N/mm]. The digital signal representing the quantity $F_2$ is transmitted to an average generator block 70, a Relative Force Processor 72 and an output port 272, In the following two steps, 154 and 155, an average distribution force $F_{2av}$ is generated by means of the average generator block 70 and then, the second step 156, calculate the scalar factor $$F_R = (F_2 - F_{2av})/F_{2av}$$

by means of a Relative Force Processor 72. The flatness vector $\Delta\sigma_1$ [N/mm$^2$] is then calculated by use of a flatness vector generator block 74 in the following step 156. The thickness vector t is used in this step 156 as an input to the generator 74. The flatness vector $\Delta\sigma_1$ is calculated by use of the formula $$\Delta\sigma_1 = F_R T/(wt)$$

One further step 157 may be taken—that is to transform the flatness vector $\Delta\sigma_1$ [N/mm$^2$] to a corresponding dimensionless quantity flatness vector $\Delta\sigma_2$ [I-unit]. The flatness vector $\Delta\sigma_1$ [N/mm$^2$] is forwarded to a E-module processor block/step 76/157 and the flatness vector $\Delta\sigma_2$ is generated as an output 280. By dividing the flatness vector $\Delta\sigma_1$ [N/mm$^2$] with the modulus of elasticity E, the corresponding dimensionless flatness vector $\Delta\sigma_2$ is generated. The FDU 56 has a flatness vector $\Delta\sigma_1$ output 274. The quantities $\Delta\sigma_1$ and $\Delta\sigma_2$ are forwarded in digital form as signals to said output ports 274 and 276 for further purposes in the rolling mill system, e.g. control and display purposes.

The method is repeated each time as new measured information from the measuring devices is received by the Flatness Distribution Unit.

Figure 5:
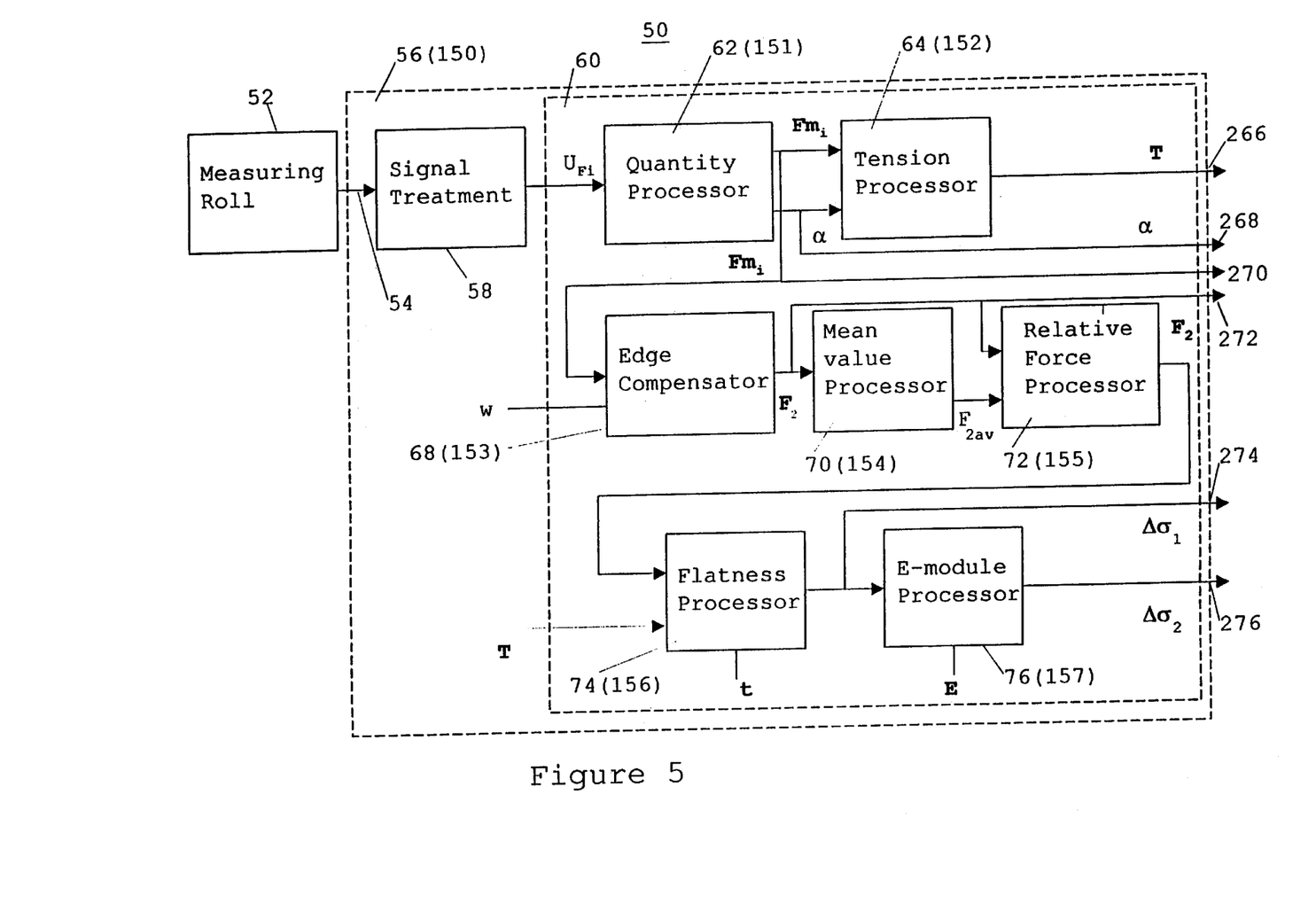
FIG. 5 is a simplified block diagram of a Flatness Determination Unit, FDU, illustrating the blocks of the system and method steps according to the invention.

The steps, blocks and the devices discussed in the embodiment according to FIG. 5 may be implemented as hardware circuits or as software routines in a processor or central processing unit, CPU. Therefore, the invention is implemented as a computer program product containing computer program code elements or software routines that when run on a computer or processor will carry out the steps of the method.

The present invention is not limited to the above-described preferred embodiments. Various alternatives, modifications and equivalents may be used. Therefore, the above embodiments should not be taken as limiting the scope of the invention, which is defined by the appended claims.

What is claimed is:

1. A system for measuring and determining flatness of a strip of rolled material, comprising: a measuring roll, having a cylindrical central structure, having a number of measuring devices for force and pressure registration, said devices generating measurement output signals ($U_{pi}$) depending on the contact between the strip and the measuring roll, said measurement output signal ($U_{pi}$) including a force component signal ($U_{F1}$), a Flatness Determination Unit, for calculating the flatness ($\Delta\sigma_1$) of the strip based exclusively on signals derived from measurement output signal ($U_{pi}$) values generated by said measuring devices and information about the values of the strip width (w) and strip thickness (t), said unit also having means for continuously determining the Wrap Angle ($\alpha$) from at least one measurement output signal ($U_{Fi}$) and means for automatically compensating for a changing Wrap Angle ($\alpha$).

2. A system according to claim 1, wherein said measurement output signals ($U_{pi}$) are input signals to the Flatness Determination Unit for calculating Wrap Angle ($\alpha$), Strip Tension (T) and Distributed Force ($F_2$).

3. A system according to claim 1, wherein the Flatness Determination Unit comprises: at least one signal processor for determining Wrap Angle ($\alpha$), Strip Tension (T) and Distributed Force ($F_2$).

4. A system according to claim 3, wherein the Flatness Determination Unit comprises: a Quantity Processor determining for each measurement channel the Wrap Angle ($\alpha$), and a Force ($Fm_i$) for each measurement zone (i, i=1,2,3, . . . ,n).

5. A system according to claim 4, wherein the Flatness Determination Unit comprises: at least one Tension Processor for determining the strip tension (T).

6. A system according to claim 5, wherein the Flatness Determination Unit comprises: at least one Edge Compensator for determining Force Distribution Vector ($F_2$.)

7. A system according to claim 6, wherein the Flatness Determination Unit comprises: at least one Mean Value Processor (70) for determining a mean value ($F_{2av}$).

8. A system according to claim 7, wherein the Flatness Determination Unit comprises: at lest one Flatness Processor for determining a Flatness Vector ($\Delta\sigma_1$).

9. A method for measuring and determining the flatness of a strip of rolled material in a system based upon the Wrap Angle ($\alpha$) of the strip on a measuring roll, said measuring roll, having a cylindrical central structure, having a number of measuring devices for force and pressure registration, said devices generating measurement output signals ($U_{pi}$) depending on the contact between the strip and the measuring roll, wherein said measurement output signal ($U_{pi}$) includes a force component signal ($U_{Fi}$), a Flatness Determination Unit for calculating the flatness ($\Delta\sigma_1$) of the strip based exclusively on signals derived from measurement output signals ($U_{pi}$) values generated by said measuring devices and information about the values of the width and thickness of the strip, wherein said method comprises the steps of:

continuously determining the Wrap Angle ($\alpha$) from at least one measurement output signal ($U_{pi}$); and automatically compensating for a changing Wrap Angle ($\alpha$).

10. A method according to claim 9, further comprising the step of:

determining for each measurement channel a Wrap Angle ($\alpha$), and a Force ($Fm_i$) for each measurement zone (i, i=1,2,3, . . . ,n) exclusively using signals derived from the measurement output signals ($U_{pi}$).

11. A method according to claim 10, comprising the step of:

determining a strip tension T using the Wrap Angle ($\alpha$), and a Force ($Fm_i$) for each measurement zone (i, i=1,2,3, . . . ,n).

12. A method according to claim 11, further comprising the step of:

determining a Force Distribution Vector ($F_2$.)

13. A method according to claim 12, further comprising: the step of:

determining a mean value ($F_{2av}$) using the Force Distribution Vector ($F_2$.)

14. A method according to claim 13, further comprising the step of:

determining Flatness Vector ($\Delta\sigma_1$) using a determined the strip tension (T) and the Force Distribution Vector ($F_2$,) which may have been scaled in a preceding step.

15. A computer program product containing computer program code elements or software routines that when run on a computer or processor will carry out the steps of a method according to claim 9.

16. A flatness determination signal for measuring and determining the flatness of a strip of rolled material and derived from at least one measurement signal ($U_{pi}$), wherein each separate measurement signal ($U_{pi}$) is generated by a corresponding measuring device of all measuring devices belonging to at least one of all measurement zones of a measuring roll and comprises one or more measurable values for calculating at least one of following quantities or vectors: strip tension vector (T,) Wrap Angle ($\alpha$) distributed force vector ($F_2$,) force vector ($F_{mi}$,) flatness vector ($\Delta\sigma_1$[N/mm$^{-2}$] and/or a corresponding quantity flatness vector ($\Delta\sigma_2$) [I-unit.]

17. A flatness determination signal according to claim 16, wherein said flatness determination signal is an input signal to a flatness determination unit for calculating at least one of said quantities or vectors.

18. A flatness determination signal according to claim 17, wherein said flatness determination signal comprises a force component signal ($U_{Fi}$).

19. A flatness determination signal according to claim 18, wherein said force component signal ($U_{Fi}$) includes a train of electrical pulses.

20. A flatness determination signal according to claim 16, wherein a number of said separate measurement signals ($U_{pi}$), each includes a train of electrical pulses, are synchronized and combined to a flatness determination signal for calculating at least one of said quantities or vectors.

21. A system for measuring and determining a flatness of a strip of rolled material, comprising: a measuring roll, having a cylindrical central structure, having a number of measuring devices for force and pressure registration, said devices generating measurement output signals ($U_{pi}$) depending on the contact between the strip and the measuring roll, said measurement output signal ($U_{pi}$) including a force component signal ($U_{pi}$), a Flatness Determination Unit, for calculating the flatness ($\Delta\sigma_1$) of the strip based exclusively on signals derived from measurement output signal ($U_{pi}$) values generated by said measuring devices and information about the values of the strip width (w) and strip thickness (t), said unit including programmable means and a computer program therefore for continuously determining the Wrap Angle ($\alpha$) from at least one measurement output signal ($U_{pi}$) and means for automatically compensating for a changing Wrap Angle ($\alpha$).

22. A system for measuring and determining a flatness of a strip of rolled material, comprising: a measuring roll, having a cylindrical central structure, having a number of measuring devices for force and pressure registration, said devices generating measurement output signals ($U_{pi}$) depending on the contact between the strip and the measuring roll, said measurement output signal ($U_{pi}$) including a force component signal ($U_{pi}$), and a signal comprising a value for a Flatness Vector according to any of ($\Delta\sigma_1$) or ($\Delta\sigma_2$) Flatness Determination Unit, for calculating the flatness ($\Delta\sigma_1$) of the strip based exclusively on signals derived from measurement output signal ($U_{pi}$) values generated by said measuring devices and information about the values of the strip width (w) and strip thickness (t), said unit also having means for continuously determining the Wrap Angle ($\alpha$) from at least one measurement output signal ($U_{pi}$) and means for automatically compensating for a changing Wrap Angle ($\alpha$).

23. A computer data signal according to claim 22, wherein the signal is superimposed on a carrier wave.

* * * * *